United States Patent
Nakazato et al.

(12)

(10) Patent No.: US 6,380,384 B1
(45) Date of Patent: Apr. 30, 2002

(54) 1,2-DIHYDRO-2-OXOQUINOLINE DERIVATIVES

(75) Inventors: Atsuro Nakazato; Taketoshi Okubo; Toshihito Kumagai; Shigeyuki Chaki; Kazuyuki Tomisawa, all of Tokyo; Masashi Nagamine, Nara; Makoto Gotoh; Masanori Yoshida, both of Osaka, all of (JP)

(73) Assignees: Taisho Pharmaceutical Co., Ltd.; Nihon Nohyaku Co., Ltd., both of (JP)

( * ) Notice: Subject to any disclaimer, the term of this patent is extended or adjusted under 35 U.S.C. 154(b) by 0 days.

(21) Appl. No.: 09/829,203

(22) Filed: Apr. 10, 2001

Related U.S. Application Data

(62) Division of application No. 09/555,568, filed on Jun. 1, 2000, now Pat. No. 6,329,525.

(30) Foreign Application Priority Data

Dec. 3, 1997 (JP) .............................................. 9-332539

(51) Int. Cl.[7] .................... C07D 401/06; C07D 401/14; C07D 403/06
(52) U.S. Cl. ..................... 544/116; 544/354; 544/357
(58) Field of Search .................. 544/116, 354, 544/357

(56) References Cited

U.S. PATENT DOCUMENTS

| | | | |
|---|---|---|---|
| 4,450,167 A | 5/1984 | Le Martret et al. .......... | 424/528 |
| 5,206,382 A | 4/1993 | Costa et al. ................ | 548/494 |
| 5,248,684 A | 9/1993 | Suzuki et al. ............... | 514/299 |
| 5,569,669 A | 10/1996 | Guillaumet et al. ......... | 514/432 |

FOREIGN PATENT DOCUMENTS

| | | |
|---|---|---|
| JP | 63-146872 | 6/1988 |
| JP | 2-152966 | 6/1990 |
| JP | 4-226980 | 8/1992 |
| JP | 6-501030 | 2/1994 |
| JP | 6-506925 | 8/1994 |
| JP | 7-278068 | 10/1995 |
| JP | 8-311033 | 11/1996 |
| WO | 92/18483 | 10/1992 |
| WO | 99/52875 | 10/1999 |

OTHER PUBLICATIONS

Angelino et al, The Oxidation of 1–Alkyl(aryl)quinolinium Chlorides..., Jan.–Feb. 1984, vol. 21, No. 1 pp. 107–112.

*Primary Examiner*—Patricia L. Morris
(74) *Attorney, Agent, or Firm*—Lorusso & Loud

(57) ABSTRACT

A 1,2-dihydro-2-oxoquinoline derivative represented by the formula:

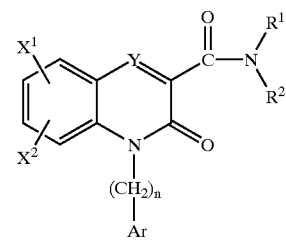

wherein Ar is a pyridyl group or a group represented by the formula:

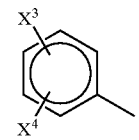

(wherein $X^3$ and $X^4$ are the same or different, and are each a hydrogen atom, a halogen atom, a $C_{1-5}$ alkyl group, a $C_{1-5}$ alkoxy group, a hydroxyl group or a trifluoromethyl group), Y is a nitrogen atom, CH or C(OH), $R^1$ and $R^2$ are the same or different, and are each a hydrogen atom, a $C_{1-10}$ alkyl group, a $C_{3-15}$ alkoxyalkyl group or a $C_{3-15}$ alkylaminoalkyl group, or $R^1$ and $R^2$ taken together with the nitrogen atom to which they are attached form a cyclic amino group, $X^1$ and $X^2$ are the same or different, and are each a hydrogen atom, a $C_{1-5}$ alkyl group, a $C_{1-5}$ alkoxy group or a halogen atom; or $X^1$ and $X^2$ taken together form an alkylenedioxy group, and n is an integer of 1 to 3; or a pharmaceutically acceptable salt thereof.

2 Claims, No Drawings

1,2-DIHYDRO-2-OXOQUINOLINE DERIVATIVES

This application is a division of U.S. Ser. No. 09/555,568 filed Jun. 1, 2000, now U.S. Pat. No. 6,329,525.

TECHNICAL FIELD

The present invention relates to compounds having a high affinity for mitochondrial diazepam binding inhibitor receptor (MDR).

BACKGROUND ART

Benzodiazepine (BZ) receptors which are an acting site of anti-anxiety drugs are classified into 2 subtypes of central benzodiazepine receptor (CBR) located on $GABA_A$ receptor/chloride channel complex and MDR located on the central nervous system (glial cells) or adrenal glands (Clin. Neuropharmacol., 16, 401–417 (1993)). Recently, CBR agonists of which representative is diazepam are widely used as anti-anxiety drugs. However, since CBR agonists act directly on $GABA_A$ receptor/chloride channel complex, they cause an anti-anxiety action together with side-effects such as excessive sedation or psychic dependence. On the other hand, since MDR agonists act indirectly on $GABA_A$ receptor/chloride channel complex via synthesis of neurosteroids such as endogenous neuroactive steroids (endogenous anti-anxiety substances), they cause an anti-anxiety action, but do not cause side-effects such as psychic dependence or excessive sedation (J. Pharmacol. Exp. Ther., 267, 462–471, 1993; ibid., 265, 649–656, 1993).

Accordingly, there is a need of the development of therapeutic agents for diseases (obsessive disorders, panic disorders) on which the previous BZs do not have a satisfactorily therapeutic effect, and development of MDR agonists as anti-anxiety drugs which alleviate the side-effects as recognized in the previous BZs.

Furthermore, the compounds which act on MDR, in view of acting on $GABA_A$ receptors, have a possibility of use as therapeutical agents of sleeping disorders, epilepsy, dyskinesia accompanied by muscle rigidity, feeding disorders, circulation disorders, recognition and learning disability or drug dependence (Progress in Neurobiology, 38, 379–395, 1992, ibid., 49, 73–97, 1996; J. Neurochem., 58, 1589–1601; Neuropharmacol., 30, 1435–1440, 1991). In addition, these compounds, in view of the physiological functions of MDR, have a possibility of use as therapeutic agents of cancer (Biochimica et Biophysica Acta, 1241, 453–470, 1995), lipid metabolism abnormality (Eur. J. Pharmacol., 294, 601–607, 1995), schizophrenia (Neuropharmacology, 35, 1075–1079, 1996), cerebral infarction (J. Neurosci., 15, 5263–5274, 1995), AIDS (Abstracts of the fifth international conference on AIDS, p. 458, 1989), Alzheimer's disease (Alzheimer Dis. Assoc. Disotd., 2, 331–336, 1988) or Huntington chorea (Brain Res., 248, 396–401, 1982).

Among the compounds having affinity for MDR, there are indole compounds disclosed in Japanese Translation of PCT publication (Kohyo) No. 6-501030.

DISCLOSURE OF THE INVENTION

As a result of extensive researches about compounds having a high affinity for MDR, the present inventors have found that the specific 1,2-dihydro-2-oxoquinoline derivatives meet the above object, thus the present invention has been accomplished. As stated above, while the indole compounds having an affinity for MDR are known, there are not reported 1,2-dihydro-2-oxoquinoline derivatives of the present invention which have an affinity for MDR.

The present invention is directed to a 1,2-dihydro-2-oxoquinoline derivative represented by Formula [I]:

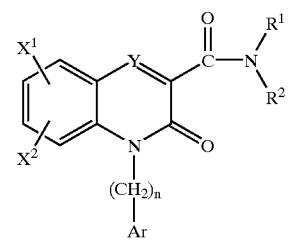

wherein Ar is a pyridyl group or a group represented by the formula:

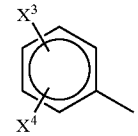

(wherein $X^3$ and $X^4$ are the same or different, and are each a hydrogen atom, a halogen atom, a $C_{1-5}$ alkyl group, a $C_{1-5}$ alkoxy group, a hydroxyl group or a trifluoromethyl group), Y is a nitrogen atom or CH, $R^1$ and $R^2$ are the same or different, and are each a hydrogen atom, a $C_{1-10}$ alkyl group, a $C_{3-15}$ alkoxyalkyl group or a $C_{3-15}$ alkylaminoalkyl group, or $R^1$ and $R^2$ taken together with the nitrogen atom to which they are attached form a cyclic amino group, $X^1$ and $X^2$ are the same or different, and are each a hydrogen atom, a $C_{1-5}$ alkyl group, a $C_{1-5}$ alkoxy group or a halogen atom, or $X^1$ and $X^2$ taken together form an alkylenedioxy group, and n is an integer of 1 to 3, provided that Y is other than CH when all of $R^1$, $R^2$, $X^1$, $X^2$, $X^3$ and $X^4$ are hydrogen atoms; or a pharmaceutically acceptable salt thereof.

In the present invention, the halogen atom for $X^3$ and $X^4$ refers to a fluorine atom, a chlorine atom, a bromine atom or an iodine atom. The $C_{1-5}$ alkyl group for $X^3$ and $X^4$ refers to a straight or branched alkyl group, and examples thereof are a methyl group, an ethyl group, a propyl group and an isopropyl group. The $C_{1-5}$ alkoxy group for $X^3$ and $X^4$ refers to a straight or branched alkoxy group, and examples thereof are a methoxy group and an ethoxy group. The $C_{1-10}$ alkyl group for $R^1$ and $R^2$ refers to a straight, branched or cyclic alkyl group, and examples thereof are a methyl group, an ethyl group, a propyl group, an isopropyl group, a cyclopropyl group, a butyl group, an isobutyl group, a cyclobutyl group, a cyclopropylmethyl group, a pentyl group, an isopentyl group, a cyclopentyl group, a cyclobutylmethyl group, a 1-ethylpropyl group, a hexyl group, an isohexyl group, a cyclohexyl group, a cyclopentylmethyl group, a 1-ethylbutyl group, a heptyl group, an isoheptyl group, a cyclohexylmethyl group, an octyl group, a nonyl group and a decyl group. The $C_{3-15}$ alkoxyalkyl group for $R^1$ and $R^2$ refers to a straight, branched or cyclic $C_{1-13}$ alkoxy-$C_{2-14}$ alkyl group, and examples thereof are a methoxyethyl group, a methoxypropyl group, a methoxybutyl group, an ethoxyethyl group, an ethoxypropyl group, an ethoxybutyl group, an ethoxypentyl group, an ethoxyhexyl group, an ethoxyheptyl group, a propoxyethyl group, a propoxypropyl group, a propoxybutyl group, an isopropoxyethyl group and a cyclopropylmethoxyethyl group. The $C_{3-15}$ alkylaminoalkyl group for $R^1$ and $R^2$ refers to a straight, branched or cyclic $C_{1-13}$ alkylamino-$C_{2-14}$ alkyl group, and examples thereof are a methylaminoethyl group, a dimethylaminoethyl group, a methylaminopropyl group, a dimethylaminopropyl group, a methylaminobutyl group, an ethylaminoethyl group, an ethylaminopropyl group, an ethylaminobutyl group, an ethylaminopentyl group, an ethylaminohexyl group, an ethylaminoheptyl group, an ethylaminooctyl group, a propylaminoethyl group, a propylaminopropyl group, a propylaminobutyl group, an isopropylaminoethyl group, a cyclopropylmethylaminoethyl group and a pyrrolidinoethyl group. Examples of the cyclic amino group which is formed by $R^1$, $R^2$ and the nitrogen atom to which they are attached are a pyrrolidino group, a piperidino group, a homopiperidino group, a morpholino group, a piperazino group, an N-methylpiperazino group and a 3,5-dimethylpiperazino group. The $C_{1-5}$ alkyl group for $X^1$ and $X^2$ refers to a straight, branched or cyclic alkyl group, and examples thereof are a methyl group, an ethyl group, a propyl group, an isopropyl group, a butyl group, an isobutyl group and a pentyl group. The $C_{1-5}$ alkoxy group for $X^1$ and $X^2$ refers to a straight, branched or cyclic alkoxy group, and examples thereof are a methoxy group, an ethoxy group, a propoxy group, an isopropoxy group, a butoxy group, an isobutoxy group, a cyclopropylmethoxy group, a pentoxy group and an isopentoxy group. The halogen atom for $X^1$ and $X^2$ refers to a fluorine atom, a chlorine atom, a bromine atom or an iodine atom. Examples of the $C_{1-5}$ alkylenedioxy group which is formed by $X^1$ and $X^2$ taken together are a methylenedioxy group, an ethylenedioxy group and an n-propylenedioxy group. In addtion, examples of the pharmaceutically acceptable salt in the present invention are salts with mineral acids such as sulfuric acid, hydrochloric acid or phosphoric acid, or salts with organic acids such as acetic acid, oxalic acid, lactic acid, tartaric acid, fumaric acid, maleic acid, methanesulfonic acid or benzenesulfonic acid.

The compound of Formula [I] can be prepared by the following general preparation methods 1 to 3. In the following reaction formulae, Ar, Y, $R^1$, $R^2$, $X^1$, $X^2$ and n are as defined above, $Y^1$ is a nitrogen atom or CH, $R^3$ and $R^4$ are the same or different, and are each a $C_{1-5}$ alkyl group or a benzyl group, and $X^5$ is a chlorine atom, a bromine atom or an iodine atom.

[General Preparation Method 1]

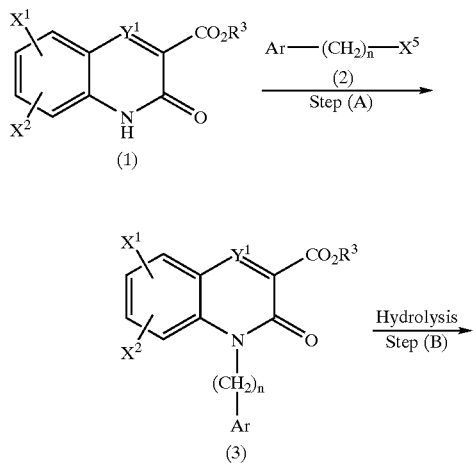

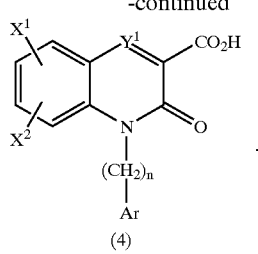
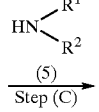

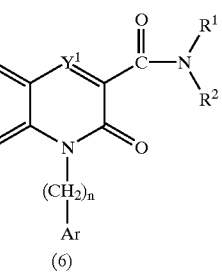

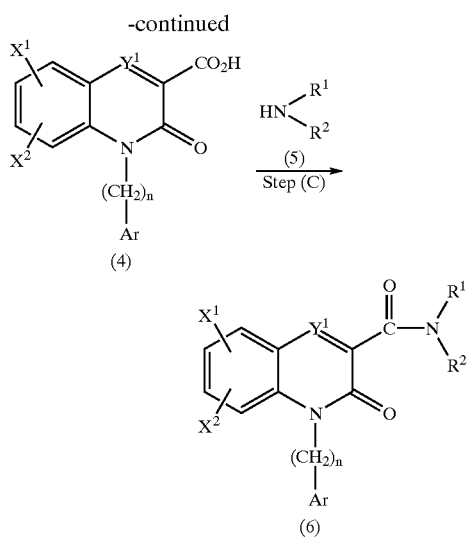

Step (A): A 1,2-dihydro-2-oxoquinolinecarboxylate ester derivative (1) can be reacted with an arylalkyl halide derivative (2) in an inert solvent, if necessary, by using a phase transfer catalyst in the presence of a base to give a 1-arylalkyl-1,2-dihydro-2-oxoquinolinecarborboxylate ester derivative (3).

Examples of the inert solvent are alcohols (e.g. methanol or ethanol), ethers (e.g. 1,2-dimethoxyethane or tetrahydrofuran), hydrocarbons (e.g. toluene or benzene), halogenide solvents (e.g. chloroform or dichloromethane), acetonitrile, N,N-dimethylformamide, water and a mixture thereof. Examples of the phase transfer catalyst are quaternary ammonium salts (e.g. benzyltriethyl ammonium bromide) and crown ethers (e.g. 18-crown-6-ether). Examples of the base are inorganic bases (e.g. potassium carbonate, sodium hydroxide, sodium hydride or metallic sodium) and alcoholates (e.g. potassium t-butoxide or sodium ethoxide).

Step (B): The 1-arylalkyl-1,2-dihydro-2-oxoquinolinecarborboxylate ester derivative (3) is hydrolyzed with a base or an acid in an inert solvent to give a 1-arylalkyl-1,2-dihydro-2-oxoquinolinecarboxylic acid derivative (4).

Examples of the inert solvent are alcohols (e.g. methanol or ethanol), ketones (e.g. acetone), ethers (e.g. 1,2-dimethoxyethane or tetrahydrofuran), hydrocarbons (e.g. toluene or benzene), halogenide solvents (e.g. chloroform or dichloromethane), acetonitrile, N,N-dimethylformamide and a mixture of these solvents with water. Examples of the base are inorganic bases (e.g. potassium carbonate, sodium carbonate, potassium hydroxide or sodium hydroxide). Examples of the acid are hydrochloric acid, sulfuric acid and phosphoric acid.

Step (C): The compound (6) of the present invention can be synthesized from the 1-arylalkyl-1,2-dihydro-2-oxoquinolinecarboxylic acid derivative (4) via the acid halide or mixed acid anhydride thereof.

The acid halide includes an acid chloride and an acid bromide, and for example, they can be obtained by reacting a halogenating agent (e.g. thionyl chloride, thionyl bromide, oxalyl chloride, carbon tetrachloride—triphenylphosphine or carbon tetrabromide—triphenylphosphine) in an inert solvent. Examples of the above inert solvent are ethers (e.g. tetrahydrofuran), hydrocarbons (e.g. toluene or benzene), halogenide solvents (e.g. chloroform or dichloromethane), acetonitrile and N,N-dimethylformamide.

The mixed acid anhydride includes an anhydride of a carboxylic acid with a carbonic acid, and for example, it can be obtained by reacting a halocarbonate ester (e.g. ethyl chlorocarbonate or isobutyl chlorocarbonate) in the presence of an organic base (e.g. triethylamine, diisopropylethylamine, N-methylmorpholine or pyridine) or an inorganic base (e.g. sodium hydride) in an inert solvent. Examples of the inert solvent are ethers (e.g. tetrahydrofuran), hydrocarbons (e.g. toluene or benzene), halogenide solvents (e.g. chloroform or dichloromethane), acetonitrile and N,N-dimethylformamide.

The compound (6) of the present invention can be also obtained by the reaction of the 1-arylalkyl-1,2-dihydro-2-oxoquinolinecarboxylic acid derivative together with a condensing agent and an amine (5) in an inert solvent.

The condensing agent refers to a conventional amidating reagent such as, for example, diphenylphosphoryl azide, diethyl cyanophosphate, carbonyldiimidazole or carbodiimides of which representatives are N,N'-dicyclohexylcarbodiimide and N-ethyl-N'-dimethylaminopropylcarbodiimide hydrochloride. Examples of the inert solvent are ethers (e.g. 1,2-dimethoxyethane or tetrahydrofuran), hydrocarbons (e.g. toluene or benzene), halogenide solvents (e.g. chloroform or dichloromethane), acetonitrile and N,N-dimethylformamide. In this reaction, if necessary, N-hydroxysuccinimide, 1-hydroxybenzotriazole, 3-hydroxy-4-oxo-3,4-dihydro-1,2,3-benzotriazine, etc. can be added as an activating agent.

[General Preparation Method 2]

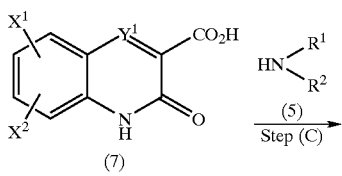

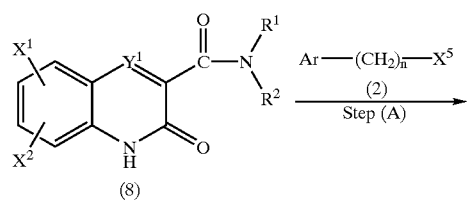

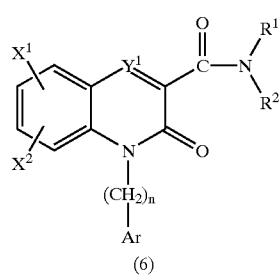

A 1,2-dihydro-2-oxoquinolinecarboxylic acid derivative (7) is amidated according to Step (C) to give a compound (8) of the present invention, which is then subjected to 1-arylalkylation according to Step (A) to give a compound (6) of the present invention.

[General Preparation Method 3]

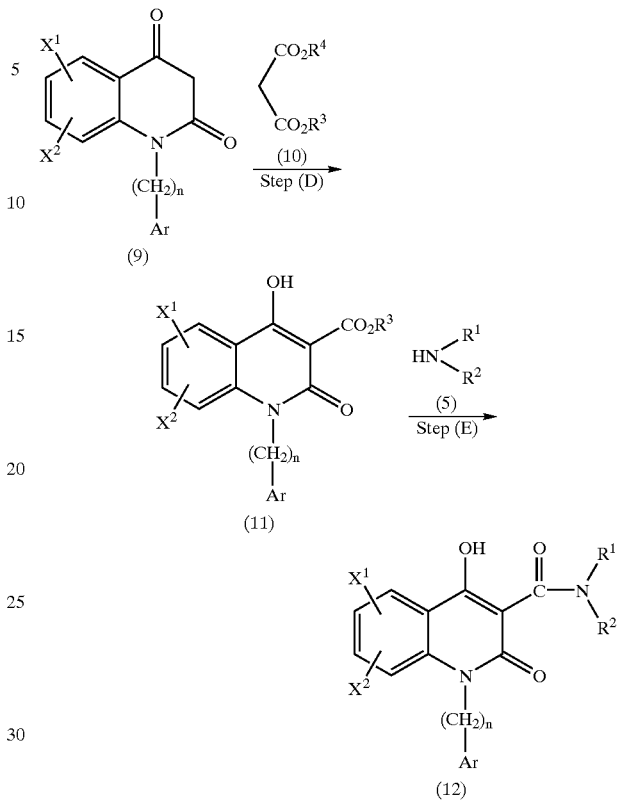

Step (D): An isatoic anhydride derivative (9) is reacted with a malonate ester (10) in an inert solvent in the presence of a base to give a 4-hydroxy-1,2-dihydro-2-oxoquinolinecarboxylate ester derivative (11).

Examples of the inert solvent are alcohols (e.g. methanol or ethanol), ethers (e.g.,1,2-dimethoxyethane or tetrahydrofuran), hydrocarbons (e.g. toluene or benzene), halogenide solvents (e.g. chloroform or dichloromethane), acetonitrile, N,N-dimethylformamide, water and a mixture thereof. The base includes inorganic bases (e.g. potassium carbonate, sodium hydroxide, sodium hydride or metallic sodium) or alcoholates (e.g. potassium t-butoxide or sodium ethoxide).

Step (E): The 4-hydroxy-1,2-dihydro-2-oxoquinolinecarboxylate ester derivative (11) can be reacted with an amine derivative (5) in an inert solvent to give a compound (12) of the present invention.

Examples of the inert solvent are alcohols (e.g. methanol or ethanol), ethers (e.g. 1,2-dimethoxyethane or tetrahydrofuran), hydrocarbons (e.g. toluene or benzene), halogenide solvents (e.g. chloroform or dichloromethane), acetonitrile, N,N-dimethylformamide, water and a mixture thereof.

INDUSTRIAL APPLICABILITY

The compounds of the present invention have a high affinity for MDR, and therefore they are useful as therapeutic or preventive drugs of central diseases such as anxiety, related diseases thereto, depression, epilepsy, sleeping disorders, recognition and learning disability or schizophrenia, dyskinesia accompanied by muscle rigidity, feeding disorders, circulation disorders, drug dependence, cancer, lipid metabolism abnormality, cerebral infarction, AIDS, Alzheimer's disease or Huntington chorea.

BEST MODE OF CARRYING OUT THE INVENTION

The present invention is illustrated in more detail by showing the following examples and an experiment.

EXAMPLE 6

(1) Preparation of N,N-dihexyl-1-benzyl-1,2-dihydro-2-oxoquinoxaline-3-carboxamide.

A solution of 3.90 g of ethyl 1,2-dihydro-2-oxoquinoxaline-3-carboxylate in 25 ml of N,N-dimethylformamide was added dropwise to a suspension of 0.79 g of 60% sodium hydride/oil in 10 ml of N,N-dimethylformamide at room temperature over 30 minutes. After stirring at room temperature for 30 minutes, 3.36 g of benzyl bromide was added dropwise over 10 minutes, followed by stirring at room temperature overnight. The reaction mixture was concentrated under reduced pressure. The residue, after addition of ethyl acetate, was washed with water, 1 N hydrochloric acid, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; hexane—ethyl acetate=10:1–2:1) and recrystallized from ethyl acetate—hexane to give 3.77 g of ethyl 1-benzyl-1,2-dihydro-2-oxoquinoxaline-3-carboxylate.

(2) To 2.00 g of ethyl 1-benzyl-1,2-dihydro-2-oxoquinoxaline-3-carboxylate were added 10 ml of ethanol and 20 ml of 10% aqueous sodium hydroxide solution, followed by stirring at room temperature for an hour. To the reaction solution was added dropwise 3 N hydrochloric acid to make acidic (pH=3.0), and the precipitated crystals were collected by filtration and washed with water and diethyl ether to give 1.73 g of 1-benzyl-1,2-dihydro-2-oxoquinoxaline-3-carboxylic acid.

(3) In 30 ml of tetrahydrofuran were dissolved 0.50 g of 1-benzyl-1,2-dihydro-2-oxoquinoxaline-3-carboxylic acid and 0.87 ml of triethylamine, and after cooling to —40° C., 0.19 ml of ethyl chlorocarbonate was added dropwise over 5 minutes. After stirring at –40° C. for 10 minutes, 0.46 ml of dihexylamine was added dropwise over 5 minutes. After stirring at –40° C. for an hour, the temperature was raised to room temperature over an hour, followed by stirring at room temperature overnight. The reaction mixture was concentrated under reduced pressure, and the residue, after addition of ethyl acetate, was washed with water, 1N hydrochloric acid, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; chloroform) and recrystallized from hexane to give 0.53 g of N,N-dihexyl-1-benzyl-1,2-dihydro-2-oxoquinoxaline-3-carboxamide.

The structures and physical property data of the present compound and the compounds prepared similarly are shown in Tables 1 and 2.

EXAMPLE 2

Preparation of N,N-dihexyl-1-(3-picolyl)-1,2-dihydro-2-oxoquinoline-3-carboxamide.

(1) In a mixture of 50 ml of tetrahydrofuran and 250 ml of N,N-dimethylformamide were dissolved 9.46 g of 1,2-dihydro-2-oxoquinoline-3-carboxylic acid and 5.06 g of N-methylmorpholine, and after cooling to –15° C., 6.83 g of isobutyl chlorocarbonate was added dropwise over 10 minutes. After stirring at –15° C. for 10 minutes, 9.73 g of dihexylamine was added dropwise over 5 minutes. After stirring at –15° C. for 4 hours and then at room temperature overnight, the reaction mixture was concentrated under reduced pressure, and the residue, after addition of ethyl acetate, was washed with water, 1N hydrochloric acid, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was recrystallized from hexane to give 13.51 g of N,N-dihexyl-1,2-dihydro-2-oxoquinoline-3-carboxamide.

(2) To a solution of 1.01 g of N,N-dihexyl-1,2-dihydro-2-oxoquinoline-3-carboxamide in 13 ml of N,N-dimethylformamide was added 136 mg of 60% sodium hydride/oil, followed by stirring at room temperature for an hour. To the reaction solution was added 434 mg of 3-picolyl chloride, followed by stirring at room temperature for 4 hours. The reaction mixture was poured into water and extracted with ethyl acetate, and the extract was washed with water, a saturated aqueous sodium bicarbonate solution and a saturated aqueous sodium chloride solution, and dried over anhydrous sodium sulfate. After removal of the drying agent by filtration, the filtrate was concentrated under reduced pressure. The residue was purified by chromatography (silica gel; Wakogel C200 (manufactured by Wako Pure Chemicals), developing solvent; hexane—ethyl acetate= 7:13–1:19) and recrystallized from ethyl acetate to give 0.47 g of N,N-dihexyl-1-(3-picolyl)-1,2-dihydro-2-oxoquinoline-3-carboxamide.

The structures and physical property data of the present compound and the compounds prepared similarly are shown in Tables 1 and 2.

EXAMPLE 3

Preparation of N,N-dihexyl-1-benzyl-4-hydroxy-1,2-dihydro-2-oxoquinoline-3-carboxamide.

(1) In a solution of 4.50 g of diethyl malonate in 20 ml of N,N-dimethylformamide was gradually added 1.10 g of 62.4% sodium hydride at room temperature, and stirring was continued at room temperature until hydrogen evolution ceased. The reaction solution was heated to 80° C., and a solution of 6.70 g of N-benzylisatoic anhydride in 20 ml of N,N-dimethylformamide was added dropwise. After the addition, the reaction mixture was stirred under heating at 120° C. for 7 hours. After cooling to room temperature, the reaction mixture was poured into ice water and washed with ethyl acetate. The aqueous phase was made acidic with 1 N hydrochloric acid, and extracted with ethyl acetate. The organic phase was washed with a saturated aqueous sodium chloride solution, and dried over anhydrous magnesium sulfate. After removal of the drying agent by filtration, the filtrate was concentrated under reduced pressure. The residue was crystallized from ethanol to give 5.88 g of ethyl 1-benzyl-4-hydroxy-1,2-dihydro-2-oxoquinoline-3-carboxylate.

(2) A mixture of 0.30 g of ethyl 1-benzyl-4-hydroxy-1,2-dihydro-2-oxoquinoline-3-carboxylate and 2 ml of dihexylamine was stirred under heating at 130° C. for 2 hours. After cooling to room temperature, to the reaction solution were added chloroform and 1 N hydrochloric acid, and the separated organic phase was washed with 1 N hydrochloric acid and water. The organic phase was dried over anhydrous magnesium sulfate. After removal of the drying agent by filtration, the filtrate was concentrated under reduced pressure. The residue was purified by chromatography ((silica gel; Merk silica gel 230-4000 mesh (Merk Co.), developing solvent; chloroform) and allowed to stand for crystallization to give 0.36 g of N,N-dihexyl-1-benzyl-4-hydroxy-1,2-dihydro-2-oxoquinoline-3-carboxamide.

The structures and physical property data of the present compound and the compounds prepared similarly are shown in Table 2.

TABLE 1

| Comp.*[1] No. | Exp.*[2] No. | $R^1$ | $R^2$ | $X^1$ | $X^2$ | Y | n | Ar | m.p. (Recry. sol.*[3]) (° C.) |
|---|---|---|---|---|---|---|---|---|---|
| 01 | 1 | H | H | H | H | CH | 1 | Ph | 229.0~231.0 (CH$_2$Cl$_2$/Hex) |
| 02 | 1 | Me | H | H | H | CH | 1 | Ph | 177.0~177.5 (AcOEt/Hex) |
| 03 | 1 | Me | Me | H | H | CH | 1 | Ph | 219.0~220.0 (AcOEt) |
| 04 | 1 | n-Pr | n-Pr | H | H | CH | 1 | Ph | 135.0~136.0 (AcOEt/Hex) |
| 05 | 1 | n-Hex | n-Hex | H | H | CH | 1 | Ph | 118.5~120.0 (AcOEt/Hex) |
| 06 | 1 | n-Dec | n-Dec | H | H | CH | 1 | Ph | 78.5~80.0 (AcOEt/Hex) |
| 07 | 1 | (CH$_3$)$_2$N(CH$_2$)$_3$ | (CH$_3$)$_2$N(CH$_2$)$_3$ | H | H | CH | 1 | Ph | 84.0~86.0 (Hex) |
| 08 | 1 | (CH$_2$CHMe)$_2$NH*[4] | | H | H | CH | 1 | Ph | 199.5~201.0 (Hex) |
| 09 | 2 | n-Hex | n-Hex | H | H | CH | 1 | 2-F—Ph | 93.0~94.0 (standing*[5]) |
| 10 | 2 | n-Hex | n-Hex | H | H | CH | 1 | 2-Cl—Ph | 108.5~109.0 (standing*[5]) |
| 11 | 2 | n-Hex | n-Hex | H | H | CH | 1 | 4-Cl—Ph | 150.0~151.0 (standing*[5]) |
| 12 | 2 | n-Hex | n-Hex | H | H | CH | 1 | 2-Br—Ph | 115.5~116.5 (standing*[5]) |
| 13 | 2 | n-Hex | n-Hex | H | H | CH | 1 | 4-Me—Ph | 145.0~146.0 (IPE) |
| 14 | 2 | n-Hex | n-Hex | H | H | CH | 1 | 2-MeO—Ph | 99.0~100.0 (standing*[5]) |
| 15 | 2 | n-Hex | n-Hex | H | H | CH | 1 | 3-MeO—Ph | 107.5~108.0 (standing*[5]) |

*[1]Compound number
*[2]Example number used for synthesis of the compound.
*[3]Recrystallization solvent: CH$_2$Cl$_2$ = dichloromethane, Hex = hexane, AcOEt = ethyl acetate, IPE = diisopropyl ether.
*[4]a 3,5-dimethylpyperazino group.
*[5]Crystallization by purification by chromatography on a silica gel column, drying and standing
In $R^1$, $R^2$ and Ar, n-Hex is an n-hexyl group, n-Dec is an n-decyl group, n-Pr is an n-propyl group and Ph is a phenyl group.

TABLE 2

| Comp.*[1] No. | Exp.*[2] No. | $R^1$ | $R^2$ | $X^1$ | $X^2$ | Y | n | Ar | m.p. (Recry. sol.*[3]) (° C.) |
|---|---|---|---|---|---|---|---|---|---|
| 16 | 2 | n-Hex | n-Hex | H | H | CH | 1 | 2,5-(MeO)$_2$—Ph | 124.0~124.5 (standing*[4]) |
| 17 | 2 | n-Hex | n-Hex | H | H | CH | 1 | 3,5-(MeO)$_2$—Ph | 94.5~95.5 (standing*[4]) |
| 18 | 2 | n-Hex | n-Hex | H | H | CH | 1 | 2-Py | 98.5~99.0 (AcOEt) |
| 19 | 2 | n-Hex | n-Hex | H | H | CH | 1 | 3-Py | 123.0~123.5 (AcOEt) |
| 20 | 2 | n-Hex | n-Hex | H | H | CH | 1 | 4-Py | 107.5~108.0 (AcOEt) |
| 21 | 2 | n-Hex | n-Hex | H | H | CH | 2 | Ph | 75.0~77.0 (Hex) |
| 22 | 1 | n-Hex | n-Hex | 6-Cl | H | CH | 1 | Ph | 145.0~146.0 (AcOEt/Hex) |
| 23 | 1 | n-Hex | n-Hex | 7-Cl | H | CH | 1 | Ph | 119.0~119.5 (AcOEt/Hex) |
| 24 | 1 | n-Hex | n-Hex | OCH$_2$O*[5] | | CH | 1 | Ph | 123.0~124.0 (AcOEt/Hex) |
| 25 | 1 | n-Hex | n-Hex | 6-OMe | 7-OMe | CH | 1 | Ph | 122.5~123.5 (AcOEt/Hex) |

TABLE 2-continued

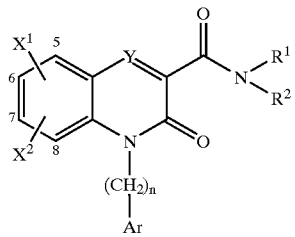

| Comp.*1 No. | Exp.*2 No. | R¹ | R² | X¹ | X² | Y | n | Ar | m.p. (Recry. sol.*3) (° C.) |
|---|---|---|---|---|---|---|---|---|---|
| 26 | 3 | n-Hex | n-Hex | H | H | COH | 1 | Ph | 106.0~108.0 (standing*4) |
| 27 | 1 | n-Hex | n-Hex | H | H | N | 1 | Ph | 53.5~55.5 (Hex) |

*1Compound number
*2Example number used for synthesis of the compound.
*3Recrystallization solvent: Hex = hexane, AcOEt = ethyl acetate.
*4Crystallization by purification by chromatography on a silica gel column, drying and standing
*5a 6,7-methylenedioxy group.
In R¹, R² and Ar, n-Hex is an n-hexyl group, Py is a pyridyl group and Ph is a phenyl group.

Experiment [MDR Receptor Binding Assay]

Crude mitochondria fractions prepared from rat cerebral cortex were used as a receptor sample, and [³H]PK11195 was used as a [³H]-labeled ligand.

A binding assay using the [³H]-labeled ligand was carried out according to the following method as described in Journal of Pharmacology and Experimental Therapeutics, 262, 971(1992).

Preparation of Receptor Sample: Rat cerebral cortex was homogenized using a Teflon-coated homogenizer in a 10 mM HEPES buffer (pH 7.4) containing 0.32 M sucrose in ten volumes of the wet weight. The homogenate was centrifuged at 900×g for 10 minutes, and the resulting supernatant was centrifuged at 9,000×g for 10 minutes. The precipitate was suspended in a HEPES buffer to give a protein concentration of 1 mg/ml, and centrifuged at 12,000×g for 10 minutes. The resulting precipitate was suspended in a 50 mM HEPES buffer (pH 7.4) to give a crude mitochondria fraction.

MDR Binding Assay:. Mitochondria sample (1.0 mg protein/ml), [³H]PK11195 (2 nM) and the test drug were reacted at 4° C. for 90 minutes.

After completion of the reaction, the reaction mixture was filtered with suction through a glass filter (GF/B) treated with 0.3% polyethyleneimine, and the radioactivity on the filter was measured by a liquid scintillation spectrometer.

The binding at the reaction in the presence of 10 μM PK11195 was defined as non-specific binding of [³H] PK11195, and the difference between total binding and non-specific binding was defined as specific binding. A fixed concentration of [³H]PK11195 (2 nM) was reacted with varied concentrations of the test drug under the above-mentioned conditions to give an inhibition curve, and the concentration (IC₅₀) of the test drug to exhibit 50% inhibition of [³H]PK11195 binding was measured by the inhibition curve, and results are shown in Table 3.

TABLE 3

| Compound No. | MDR IC$_{50}$ (nM) |
|---|---|
| 04 | 1.71 |
| 05 | 0.159 |

TABLE 3-continued

| Compound No. | MDR IC$_{50}$ (nM) |
|---|---|
| 06 | 53.4 |
| 18 | 0.404 |
| 19 | 0.368 |
| 20 | 0.192 |
| 21 | 6.58 |
| 23 | 0.132 |

What is claimed is:
1. A 1,2-dihydro-2-oxoquinoline compound represented by the formula:

wherein Ar is a pyridyl group or a group represented by the formula:

(wherein $X^3$ and $X^4$ are the same or different, and are each a hydrogen atom, a halogen atom, a $C_{1-5}$ alkyl group, a $C_{1-5}$ alkoxy group, a hydroxyl group or a trifluoromethyl group), Y is a nitrogen atom $R^1$ and $R^2$ are the same or different, and are each a hydrogen atom, a $C_{1-10}$ alkyl group, a $C_{3-15}$ alkoxyalkyl group or a $C_{3-15}$ alkylaminoalkyl group, or $R^1$ and $R^2$ taken together with the nitrogen atom to which they are attached form a cyclic amino group, $X^1$ and $X^2$ are the same or different, and are each a hydrogen atom, a $C_{1-5}$ alkyl group, a $C_{1-5}$ alkoxy group or a halogen atom, or $X^1$ and $X^2$ taken together from an alkylenedioxy group, and n is an integer of 1 to 3; or a pharmaceutically acceptable salt thereof.

2. A 1,2-dihydro-2-oxoquinoline compound represented by the formula:

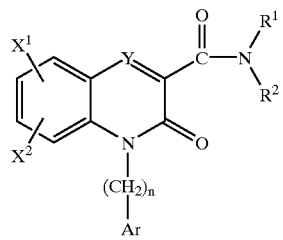

wherein Ar is a pyridyl group or a group represented by the formula:

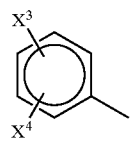

(wherein $X^3$ and $X^4$ are the same or different, and are each a hydrogen atom, a halogen atom, a $C_{1-5}$ alkyl group, a $C_{1-5}$ alkoxy group, a hydroxyl group or a trifluoromethyl group), Y is a nitrogen atom, $R^1$ and $R^2$ are the same or different, and are each a $C_{1-10}$ alkyl group, a $C_{3-15}$ alkoxyalkyl group or a $C_{3-15}$ alkylaminoalkyl group, or $R^1$ and $R^2$ taken together with the nitrogen atom to which they are attached form a cyclic amino group, $X^1$ and $X^2$ are the same or different, and are each a hydrogen atom, a $C_{1-5}$ alkyl group, a $C_{1-5}$ alkoxy group or a halogen atom, or $X^1$ and $X^2$ taken together form an alkylenedioxy group, and n is an integer of 1 to 3; or a pharmaceutically acceptable salt thereof.

* * * * *

UNITED STATES PATENT AND TRADEMARK OFFICE
CERTIFICATE OF CORRECTION

PATENT NO. : 6,380,384 B1
DATED : April 30, 2002
INVENTOR(S) : Nakazato et al.

It is certified that error appears in the above-identified patent and that said Letters Patent is hereby corrected as shown below:

<u>Title page,</u>
Item [62], Related U.S. Application Data, "[62], Division of application No. 09/555,568, filed on Jun. 1, 2000, now Pat. No. 6,329,525." should read -- [62] Division of application No. 09/555,568, filed on Jun. 1, 2000 (371 Date, and PCT filed December 3, 1998), now Pat. No. 6,329,525. --

Signed and Sealed this

Fifteenth Day of October, 2002

*Attest:*

*Attesting Officer*

JAMES E. ROGAN
*Director of the United States Patent and Trademark Office*